(12) United States Patent
Wellborn et al.

(10) Patent No.: US 11,974,889 B2
(45) Date of Patent: May 7, 2024

(54) VARIABLE RIGIDITY, CONFORMABLE APPARATUS FOR NON-INVASIVELY AFFIXING SURGICAL FIDUCIALS AND SURGICAL TOOLS TO PATIENTS

(71) Applicant: Vanderbilt University, Nashville, TN (US)

(72) Inventors: Patrick Wellborn, Nashville, TN (US); Robert J. Webster, III, Nashville, TN (US); Ray Lathrop, Indianapolis, IN (US); Richard J. Hendrick, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 1401 days.

(21) Appl. No.: 16/347,634

(22) PCT Filed: Nov. 7, 2016

(86) PCT No.: PCT/US2016/060812
§ 371 (c)(1),
(2) Date: May 6, 2019

(87) PCT Pub. No.: WO2018/084869
PCT Pub. Date: May 11, 2018

(65) Prior Publication Data
US 2019/0314112 A1  Oct. 17, 2019

(51) Int. Cl.
*A61B 90/50* (2016.01)
*A61B 17/00* (2006.01)
(Continued)

(52) U.S. Cl.
CPC .............. *A61B 90/50* (2016.02); *A61B 90/14* (2016.02); *A61B 90/39* (2016.02);
(Continued)

(58) Field of Classification Search
CPC ......... A61B 90/50; A61B 90/14; A61B 90/39; A61B 2017/00566; A61B 2034/2055;
(Continued)

(56) References Cited

U.S. PATENT DOCUMENTS 4,969,471 A * 11/1990 Daniel ................... A61B 5/103
600/595
6,226,820 B1 * 5/2001 Navarro ............... A47C 27/088
5/655.4

(Continued)

OTHER PUBLICATIONS

International Search Report and Written Opinion dated Dec. 16, 2016 for corresponding International Application No. PCT/US2016/060812.

*Primary Examiner* — Katherine H Schwiker
*Assistant Examiner* — Nasheha Baset
(74) *Attorney, Agent, or Firm* — TAROLLI, SUNDHEIM, COVELL & TUMMINO L.L.P.

(57) ABSTRACT

An apparatus for supporting a medical device on a patient includes a mounting structure configured to be fitted onto the patient to encircle at least a portion of a body part of the patient. The mounting structure includes an inner layer and an outer layer that define a confinement. A jamming material is contained within the confinement. The jamming material is configured to flow within the confinement to conform to the shape of the body part of the patient onto which the mounting structure is fitted. The mass of jamming material is configured to harden and become rigid in its conformed shape in response to a vacuum being formed in the confinement.

26 Claims, 8 Drawing Sheets

(51) Int. Cl.
  *A61B 34/20* (2016.01)
  *A61B 90/00* (2016.01)
  *A61B 90/14* (2016.01)

(52) U.S. Cl.
  CPC ............ *A61B 2017/00566* (2013.01); *A61B 2034/2055* (2016.02); *A61B 2090/3983* (2016.02); *A61B 2090/3991* (2016.02); *A61B 2090/502* (2016.02)

(58) Field of Classification Search
  CPC .... A61B 2090/3983; A61B 2090/3991; A61B 2090/502; A61B 2090/5025; A61B 2090/508; A61B 90/53; A61B 2090/506; A61B 90/57; A61B 2090/571; A61B 2090/504; A61B 2090/3954; A61B 2090/363; A61B 90/10; A61B 2090/103; A61B 2090/101; A61B 2017/00561; A61B 2017/00535; A61B 2017/00539; A61B 2017/00544; A61B 2017/00557; A61B 2034/105; A61B 2017/00876; A61B 2017/00862; A61B 2017/00831; A61B 2017/00309; A61B 2017/00305; A61B 2017/00292; A61B 2017/00238; A61B 17/00234; A61B 1/00147; A61B 1/00148; A61B 2018/00321

See application file for complete search history.

(56) References Cited

U.S. PATENT DOCUMENTS 6,355,049 B1 * 3/2002 Gill ........................ A61B 90/14
  5/622
  6,529,765 B1 * 3/2003 Franck ................... A61B 90/10
  606/130
  2007/0295604 A1 * 12/2007 Freydina ................ B01D 61/48
  204/627
  2011/0275906 A1 11/2011 Chen
  2012/0266898 A1 * 10/2012 Vogele .................... A61B 90/17
  128/869
  2016/0106508 A1 * 4/2016 Lathrop ................. A61B 90/39
  606/130
  2017/0156913 A1 * 6/2017 Islava ................. A61F 5/05883

* cited by examiner

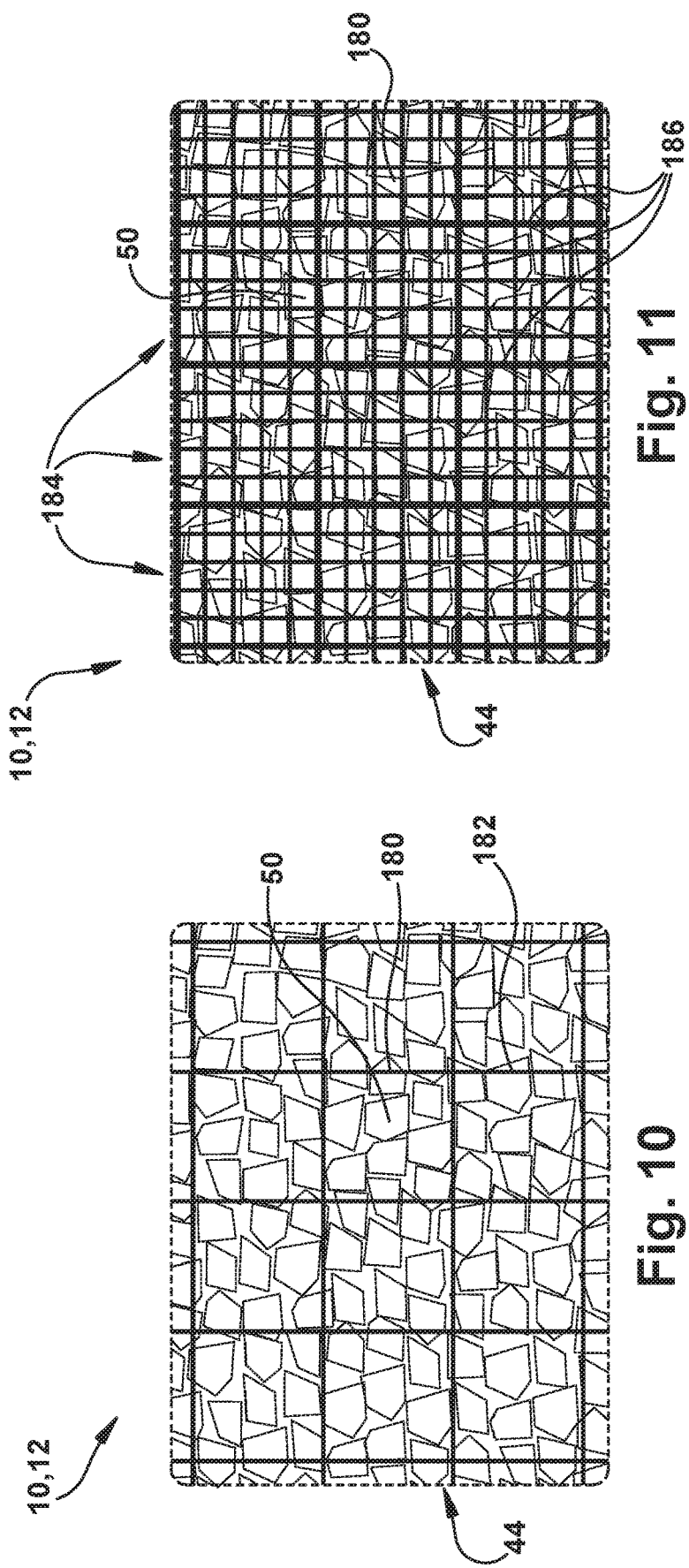

VARIABLE RIGIDITY, CONFORMABLE APPARATUS FOR NON-INVASIVELY AFFIXING SURGICAL FIDUCIALS AND SURGICAL TOOLS TO PATIENTS

STATEMENT REGARDING FEDERALLY SPONSORED RESEARCH

This invention was made with government support under grant No. R01 EB017467 awarded by the National Institutes of Health. The Government has certain rights in this invention.

TECHNICAL FIELD

The invention relates to surgical procedures that employ the use of patient mounted structures for the purpose of providing surgical tool support and/or assisting in image-based guidance. More particularly, the invention relates to a variable rigidity, conformable device for non-invasively affixing surgical fiducials and surgical tools to patients during a surgical procedure, wherein the device incorporates a jamming structure to secure the fiducials and tools to the patient.

BACKGROUND

Some surgical procedures employ the use of surgical tools that are mounted on the patient's anatomy. For example, some surgical procedures, such as endonasal procedures or eye surgery procedures, can employ the use of robotic or manually operated tools, such as endoscopes for viewing the surgical field or probes having various tool ends (e.g., forceps, graspers, cutters, curettes, dissectors, scalpels, scissors, needles, drug delivery devices, ablation elements, drills, bone punches, suction/irrigation, etc.) that are mounted on the patient's head. Patient mounted surgical tools require a stable, reliable, and rigid mounting structure to ensure that the tool mount does not move relative to the patient in during use. These relative movements are undesirable because they can lead to errors, especially in the case of surgical robots, whose accuracy and precision depend on maintaining stable positioning of the mounting structure.

During image guided surgery of the skull, the location of the head is tracked by an optical tracking system that employs means, such as a stereoscopic camera, to determine the location of optical tracking fiducials. Tracking fiducials mounted to the patient's head allow the tracking system to identify and follow the location of the patient's head. Fiducials mounted to a surgical tool, such as a probe, allow the tracking system to identify and follow the location of the tool, particularly the tip of the tool. It is very important that, once registered, the positions of the fiducials relative to the structures to which they are mounted (i.e., the head or the surgical tool) do not change. If this happens, the resulting registration errors will cause the optical tracking system to provide erroneous indications of the location of the tool relative to the patient anatomy.

Fiducials are connected to the surgical tool via a rigid mechanical connection that is extremely reliable and therefore not prone to post-registration movement that produces registration errors. Current methods and devices for attaching fiducials to the patient's head/skull are less reliable and can be prone to post-registration movement relative to the patient's head. This relative movement produces registration errors that affect the accuracy of the image navigation system and can compromise the safety of the patient. It is therefore important to minimize or eliminate relative motion between the head/skull and the tracking fiducials attached thereto. While surgically mounting the fiducial directly to the patient's bone structure is effective in helping to minimize registration errors, this attachment method is not ideal since it necessitates an additional surgical procedure, which introduces unwanted complexity and risks.

Accurate registration of the images to the patient anatomy is essential to enable the optical tracking system to accurately represent tool position with respect to the patient anatomy in general and, more specifically, to target(s) in the anatomy. Target Registration Error ("TRE") is related to Fiducial Localization Error ("FLE") and Fiducial Registration Error ("FRE"). This relationship, however, is based on the assumption that there is a rigid connection between the bone of the patient's head and the fiducials tracked by the image guidance system. Theoretical calculations show that, if used properly, clinical image guidance systems should be expected to provide very low TRE, i.e., should be highly accurate. Yet, anecdotally, surgeons report that sometimes errors are much higher than expected. Errors in these cases can reach several millimeters at the skull base. These errors are not insignificant given that surgeons often must work within closer proximity to delicate anatomical structures, such as the optic nerves and carotid arteries.

There are several different registration techniques that can be utilized in conventional clinical image guidance systems. Examples of these techniques include stereotactic frame registration, point-based registration, and surface-based registration. Stereotactic frames employ rigid frames that are fixed to the patient typically via clamps and bars. Stereotactic frames are known to have a TRE of 1-2 mm. Bone-screw-based fiducial markers are surgically fixed directly to the patient's bone structure and are known to have a TRE of 1-1.5 mm. Skin-affixed fiducials are connected to the patient's skin, e.g., via adhesive, and are known to have a TRE of 1.3-4 mm. Surface-based registration employs surface scanning techniques to establish registration and is known to have a TRE of 2-5 mm.

In endonasal surgery, stereotactic frames and bone screw-based fiducial markers are typically avoided due to their invasiveness. Due to this, non-invasive surface-based registration is employed. For example, the Kolibri® system manufactured by Brainlab AG of Feldkirchen, Germany, is an image-guided system that uses points collected from the brow and bridge of the nose (i.e. a "browscan") for registration. The location of the patient's head as well as the location(s) of the surgical tools are then tracked in real time by a stereo camera system that observes fiducials attached to each throughout the surgery. This enables the image guidance system to perform its function of showing the location of the tip of each tracked surgical tool with respect to registered preoperative images during the surgery.

According to this surface-based registration procedure, fiducial markers are supported on a rigid body that is attached to the skin of the patient's forehead using double sided foam tape and an elastic strap that wraps around the patient's head. A laser scanner is used to scan the surface of the brow which is then used by the optical tracking system to establish the shape and location of the brow and thus the skull. At the same time the scan is being performed, the optical tracking system locates the fiducials. It is assumed the rigid body and brow will not move relative to one another. Thus, the location of the skull is based on the location of the fiducial once the scan is complete, i.e., the fiducial is registered relative to the skull.

Any post-registration movement of the fiducial relative to the patient's head results in a TRE. This can occur, for example, where hospital staff accidentally bump into the rigid body, when the patient's head is repositioned during surgery, or where the staff lacks the training and understanding to appreciate the delicacy of the system when handling the patient and/or the equipment. Since the tracking rigid body is typically affixed to the head using the aforementioned adhesive and elastic headband, care must be taken to avoid displacing the skin relative to the skull or bumping the rigid body. Prior work has shown that human skin can shift in the range of 1.3-13.1 mm, with a mean of 5.34±2.65 mm under load. A previous report of 35 sinus surgery cases found movement of the headband in 14% of cases, indicating that improved fixation methods are needed. Registration accuracy depends strongly on careful fixation of the rigid body, and thus the tracking fiducial, to the patient.

SUMMARY

According to one aspect, an apparatus for fixing a support structure for a surgical tool or tracking fiducial to a patient is based on the physical properties of jammed systems. More specifically, the apparatus employs the use of a jamming material in a mounting structure that is used to help secure the support structure to the patient. In one example, the jamming material is a granular jamming material incorporated in a mounting structure that is used to help secure the support structure to a patient's head.

Under the granular jamming approach, mounting structure includes a granular substance, such as granular silica, in a container or confinement constructed of a flexible deformable material, such as a plastic/polymer material or a rubber material, that is both strong and substantially airtight. In one instance, the granular jamming substance can have a consistency similar to that of coffee grounds. In fact, the granular substance is not limited to silica granules. The granular substance can also be plastic beads, polymer beads, ceramic structures, glass structures, or even actual coffee grounds The granular jamming mounting structure supports a surgical tool (in the case of a surgical tool mount) or a rigid body and target fiducials (in the case of a target fiducial mount). When the mounting structure is positioned on the patient's head, the granular jamming substance acts like a fluid and conforms to the specific anatomy of the head. While held in position, a vacuum is drawn on the mounting structure, which collapses the confinement in which the granular jamming substance is contained. This causes the granular substance to jam together, causing the granular mass to harden and act like a solid.

The mass of granular jamming material, when hardened in response to the vacuum, is custom fitted to the exact contour of the patient's head. Thus, by arranging the confinement encompass or encircle a substantial portion of the patient's head, the hardened mass can create an interference fit with the head that can maintain the support structure, and any surgical tools or target fiducials mounted thereon, in a precisely fitted and maintained position on the patient's head.

According to one aspect, the confinement in which the granular jamming material is contained is in the form of a concave cap structure including inner and outer cap layers that are positioned nested one inside the other and interconnected about the peripheries of their respective openings. The granular jamming material is contained between the cap layers. Advantageously, the cap layers, especially the inner cap layer, can be constructed of an elastic material or a material containing an elastic component, so that the mounting structure can be secured to the patient's head by elastic constriction. For instance, the cap layers can be constructed, both in material and configuration, similarly or identical to a common swim cap. When applied, the inner cap will adhere to the patient's head in the same manner a swim cap adheres. When the vacuum is applied, the granular jamming material with harden, creating a rigid shell that bolsters the elastic retention of the inner cap layer. Advantageously, the inner cap layer can help provide a high degree of frictional engagement with the patient's head which further improves the rigidity and reliability with which the mounting structure secures the support structure to the patient.

According to another aspect, an apparatus for supporting a medical device on a patient includes a mounting structure configured to be fitted onto the patient to encircle at least a portion of a body part of the patient. The mounting structure includes an inner layer and an outer layer that define a confinement. A jamming material is contained within the confinement. The jamming material is configured to flow within the confinement to conform to the shape of the body part of the patient onto which the mounting structure is fitted. The mass of jamming material is configured to harden and become rigid in its conformed shape in response to a vacuum being formed in the confinement.

According to another aspect, alone or in combination with any preceding aspect, the inner layer can be positioned within an inner space defined by the outer layer. Overlying peripheral edge portions of the inner and outer layers can be interconnected to seal the jamming material in the confinement.

According to another aspect, alone or in combination with any preceding aspect, the inner and outer layers can be constructed of a substantially airtight material. The airtight material can be a material that is at least one of elastomeric and deformable, particularly latex or silicone rubber.

According to another aspect, alone or in combination with any preceding aspect, the inner layer of the mounting structure can be constructed of a deformable material that conforms to the patient's anatomy when fitted onto the patient.

According to another aspect, alone or in combination with any preceding aspect, the outer layer of the mounting structure can be constructed of a material that applies an inward elastic force that causes the jamming material to conform to the shape and contour of the body part onto which the mounting structure is fitted.

According to another aspect, alone or in combination with any preceding aspect, the mounting structure can be adapted to be fitted onto a patient's head.

According to another aspect, alone or in combination with any preceding aspect, the jamming material can be a granular jamming material. The granular jamming material can be at least one of silica granules, plastic beads, polymer beads, ceramic structures, glass structures, and coffee grounds.

According to another aspect, alone or in combination with any preceding aspect, the jamming material can be overlying sheets of material. The sheets of material comprise at least one of paper, sandpaper, and thin plastic sheets. The sheets of material can be strips of material arranged in a multilayer loop. The multilayer loop can extend around an annular rim portion of the mounting structure. The sheets of material can be arranged in overlying sheets arranged to form a multilayer dome of sheet material.

According to another aspect, alone or in combination with any preceding aspect, the apparatus can include a support structure adapted to receive and support the medical device. The support structure can have a portion disposed in the jamming material in the confinement so that the jamming material provides a hard, rigid support of the support device in response to the vacuum being formed in the confinement. The support structure can include a structure for supporting one or more target fiducials for an optical scanning system. The support structure can include a structure for holding a surgical tool comprising at least one of an endoscope, a drill, a probe, forceps, graspers, cutters, curettes, dissectors, scalpels, scissors, needles, drug delivery devices, ablation elements, bone punches, and suction/irrigation devices. The support structure can include a frame structure disposed within the confinement and having portions surrounded by the granular jamming material.

According to another aspect, alone or in combination with any preceding aspect, the medical device can be adapted to be fixed directly to an outer surface of the outer layer by at least one of bonding the medical to the outer surface with an adhesive and embedding the medical device to the outer layer. In this instance, the medical device can include a target fiducial.

According to another aspect, alone or in combination with any preceding aspect, the apparatus can also include a mesh material disposed in the confinement and at least partially surrounded by the granular material. The mesh material can have an open mesh size larger than the grain size of the granular material. The mesh material can have an open mesh size smaller than the grain size of the granular material, and can be compartmentalized to define compartments that contain the granular material.

According to another aspect, alone or in combination with any preceding aspect, the apparatus can further include a flexible elongated member, such as a strap, for helping to secure the mounting structure to the patient. The mounting structure can include a slit extending vertically from a rim of the mounting structure. The flexible elongated member can extend across the slit and draw portions of the mounting structure on opposite sides of the slit together.

According to another aspect, alone or in combination with any preceding aspect, the mounting structure can be a cap. The inner layer can be an inner cap layer. The outer layer can be an outer cap layer. The inner cap layer and outer cap layer each can have a concave structure. The inner cap layer can be positioned within an inner space defined by the outer cap layer. Overlying peripheral edge portions of the inner and outer cap layers can be interconnected to seal the jamming material in the confinement.

DRAWINGS

FIGS. 8-11 illustrate example configurations of mounting apparatuses that implement additional or alternative jamming structures and jamming structure features.

DESCRIPTION

The invention relates to surgical procedures that employ the use of patient mounted structures for the purpose of providing surgical tool support and/or assisting in image-based guidance. More particularly, the invention relates to an apparatus for mounting a support structure for supporting a medical device on a patient.

Figure 1:
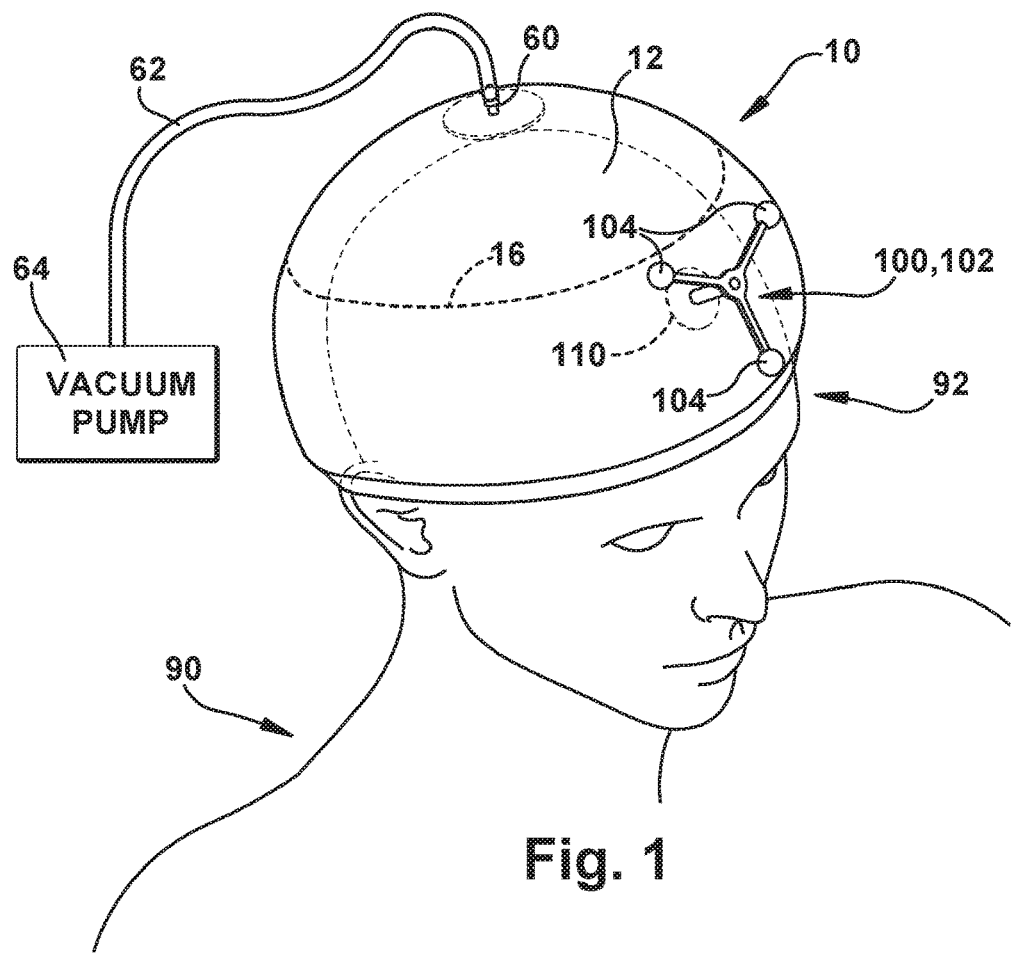
FIG. 1 is a perspective view of an apparatus for mounting a support structure on a patient using a jamming structure, according to an example configuration.
Figure 2:
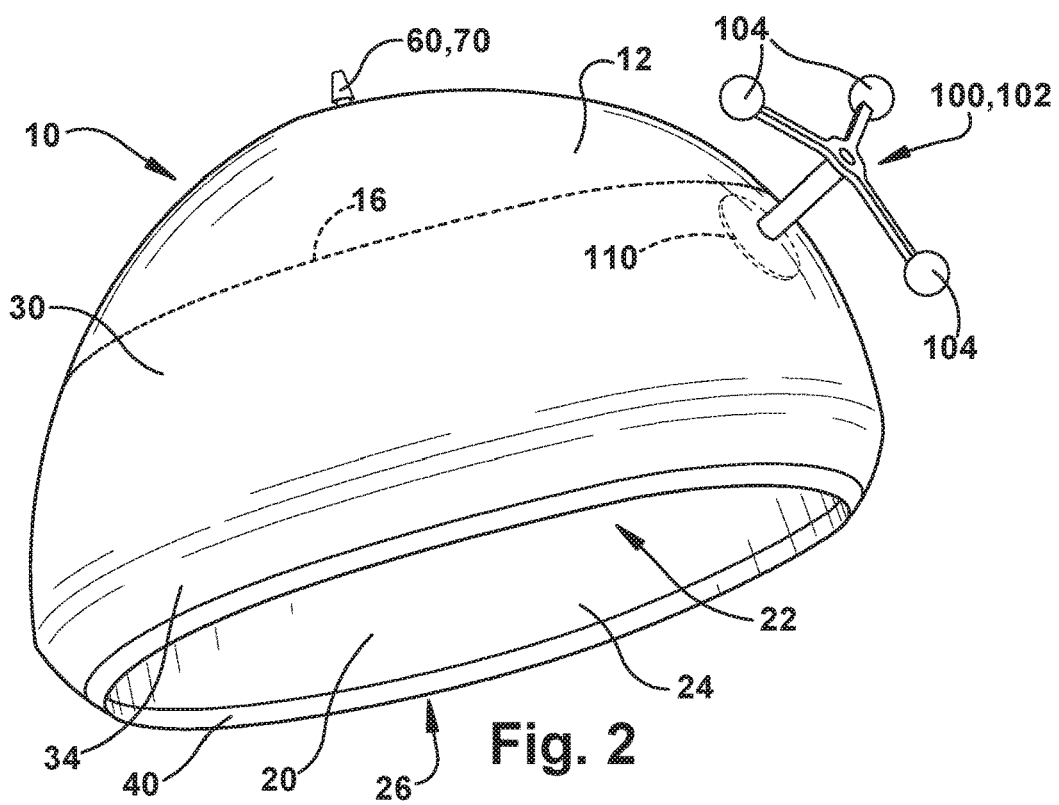
FIG. 2 is a perspective view of the mounting apparatus from a different perspective.

The mounting apparatus can be used to secure a support structure to various locations on a patient's anatomy. One particular anatomical structure for which the mounting apparatus can be particularly well-suited is the patient's head. Additionally, the support structure secured to the patient by the mounting apparatus can be adapted to support a variety of medical devices on the patient, such as tools for performing surgical procedures or optical tracking fixtures for use in image guided surgical procedures. Referring to FIGS. 1-2, according to one example configuration, the mounting apparatus 10 mounts a support structure 100 to the head 92 of a patient 90.

In the example configuration of FIGS. 1-2, the mounting apparatus 10 includes a mounting structure 12 that encircles a portion of the patient's head 92. In FIGS. 1-2, the mounting structure encircling the portion of the patient's head takes the general form of a cap 12 having a generally domed configuration for covering a generally domed portion, i.e., the cranium, of the patient's head 92. The mounting structure 12 could, however, have different forms. For example, the mounting structure 12 could take the form of a band having a predetermined width selected to encircle a corresponding portion of the patient's head 92. This is indicated generally by the dashed lines at 16 in FIGS. 1-2. In this instance, for example, the mounting structure 12 could be configured as a band that extends around the patient's head 92 and covers the patient's forehead area. Advantageously, a configuration where the mounting structure 12 is in the form of a band can be used as a mount for other portions of the patient's anatomy, such as the arms, legs, or torso.

In the example configuration of FIGS. 1-2, the mounting cap 12 includes an inner cap layer 20 and an outer cap layer 30. The inner cap layer 20 has a concave configuration defining an interior space 22 of the cap 12 and a periphery 24 that defines an opening 26 of the cap. The outer cap layer 30 has a concave configuration defining an interior space and a periphery 34. The inner cap layer 20 is positioned in the interior space of the outer cap layer 30 so that their respective peripheries 24, 34 overlie each other. To achieve this, the inner and outer cap layers 20, 30 can be similar in shape with dimensions selected so that the inner cap layer fits easily within the interior space of the outer cap layer.

With the inner cap layer 20 positioned within the interior space of the outer cap layer 30, an airtight or substantially airtight connection interconnects the overlying peripheries 24, 34 of the layers forming an airtight or substantially airtight sealed seam 40. This airtight connection can be formed, for example, by any of the following methods, either individually or in combination: stitching, bonding agents (e.g., glue, epoxy), tapes (e.g., double sided bonding tape, seal tape), ultrasonic welding, and heat bonding. Any other suitable method can be used to form the connection.

The inner and outer cap layers 20, 30 are constructed of an airtight or substantially airtight material that is generally deformable and elastic, such as a plastic, polymer, or rubber material. In one example, the cap layers 20, 30 can be constructed of latex rubber. Alternative materials could be used. The material used to construct the layers 20, 30 can exhibit a high coefficient of friction with human skin.

Figure 3A:
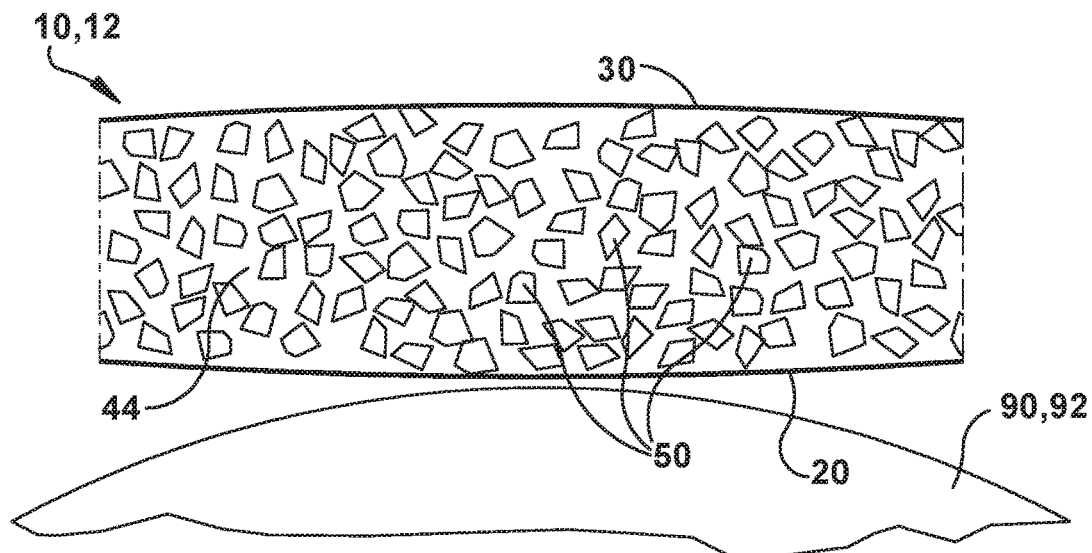
FIGS. 3A-3C are schematic illustrations of a portion of the mounting apparatus in different conditions.
Figure 3B:
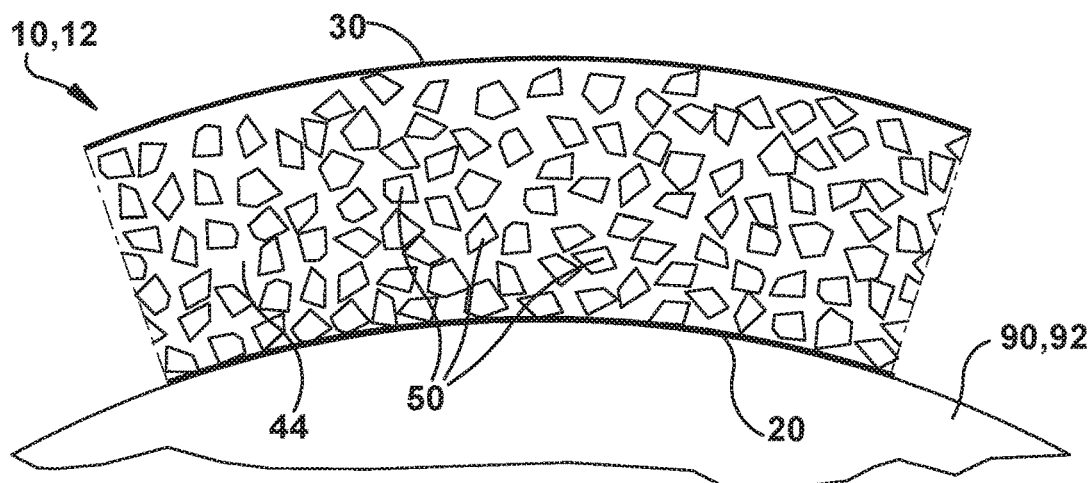
Figure 3C:
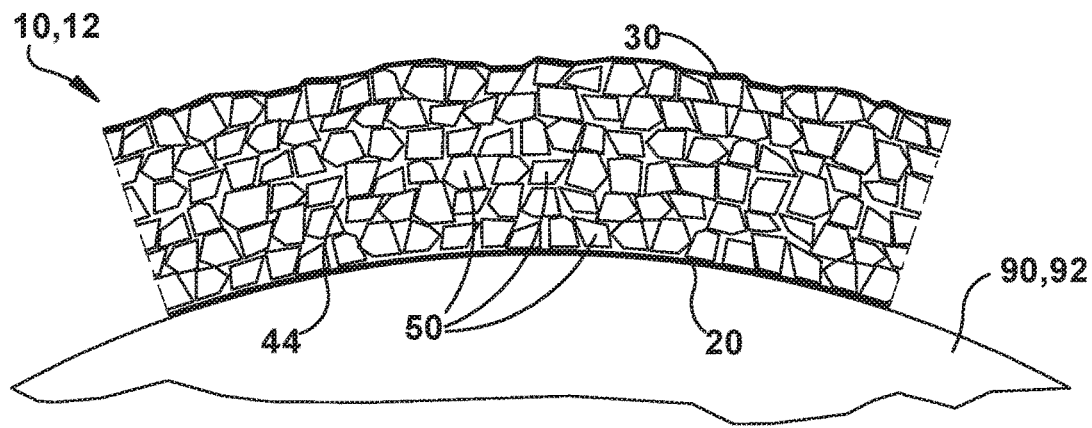

Referring to FIGS. 3A-3C, with the peripheries 24, 34 interconnected along the sealed seam 42, a space or confinement 44 of the mounting cap 12 is defined between the inner and outer cap layers 20, 30. The mounting cap 12 includes a jamming substance 50 that occupies and fills or substantially fills the space of the confinement 44 between the inner and outer cap layers 20, 30. In the example configuration of FIGS. 1-5, the jamming substance 50 can be a granular jamming substance, such as a granular silica, plastic or polymer beads, ceramic structures, glass structures, and even coffee grounds. Obviously, the granular jamming substance 50 is placed in the confinement 44 prior to applying the connection to form the seam 40.

The mounting cap 12 also includes a port 60 that provides fluid communication with the confinement 44. The port 60 extends through the outer cap layer 30 and is secured to the outer cap layer in an airtight manner. The port 60 is configured to receive a conduit 62, such as a hose, that is connected to a vacuum source 64, such as a pump. Through operation of the vacuum pump 64, a vacuum can be drawn in the confinement 44 through the vacuum port 60. The port 60 can also be installed prior to applying the connection that forms the seam 40. Although the cap 12 of the example embodiments illustrated herein includes a single vacuum port 60, it will be appreciated that the cap can include multiple spaced apart vacuum ports. Additionally, the vacuum port 60 can be located at any desired position on the cap 12.

Figure 4A:
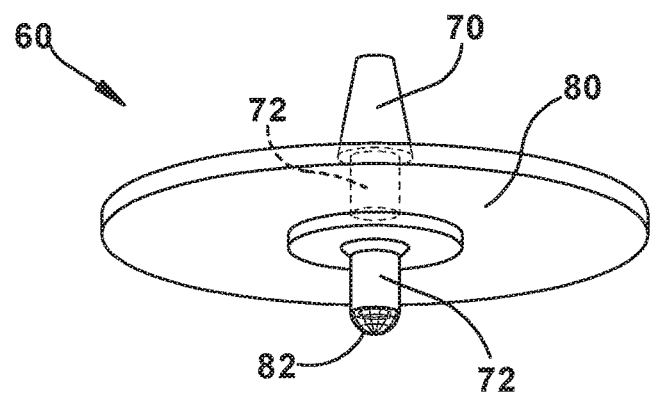
FIGS. 4A and 4B illustrate a connection port for applying a vacuum to the mounting apparatus.
Figure 4B:
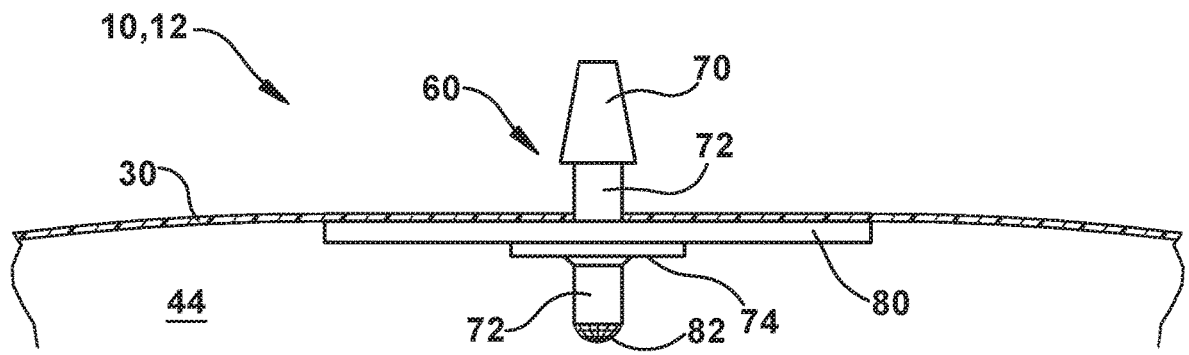

One example configuration of the vacuum port 60 is illustrated in FIGS. 4A and 4B. Referring to FIGS. 4A and 4B, the vacuum port 60 includes a nipple or hose fitting 70 for receiving the vacuum hose 62. The hose fitting 70 has a tapered configuration that allows it to be inserted through an aperture in the outer cap layer 30. A stem portion 72 of the vacuum port 60 extends through the outer cap layer 30 and includes a disc shaped flange or fixture 74 that extends radially from the stem. A gasket 80 is positioned on a surface of the fixture 74 presented toward the hose fitting 70. The gasket 80 is circular and disc-shaped having a diameter greater than that of the fixture 74. The gasket 80 can be secured and/or sealed to the fixture 74, for example, via silicone or other sealant/adhesive. At the end of the stem 72, a gas permeable barrier 82, such as felt or a screen, blocks the passage of solids and particulates, but permits the passage of gases, through the vacuum port 60.

The vacuum port 60 is secured to the outer cap layer 30 by passing the hose fitting 70 through an aperture in the outer cap layer, from the inside out, so that the hose fitting projects from the outer surface of the outer cap layer. In doing so, the gasket 80 is positioned against the inner surface of the outer cap layer 30. The outer cap layer 30 and the gasket 80 can be secured and/or sealed to each other, for example, via a sealant/adhesive, such as silicone. The outer cap layer 30 is thus positioned between the gasket 80 and a flange surface 76 of the hose fitting 70.

In another example configuration, the vacuum port 60 can be connected to the cap 12 by positioning the gasket 80 and flange 74 can be outside the confinement 44. In this configuration, the stem 72 would protrude through the outer cap layer 30 as shown in FIG. 4B. The flange 74 would be positioned against the outer surface of the outer cap layer 30 and the gasket 80 would overly the flange. The gasket could be connected to the outer cap layer via sealant or adhesive, such as a silicone adhesive, to connect the gasket and the vacuum port 60 to the outer cap layer 30.

Figure 5B:
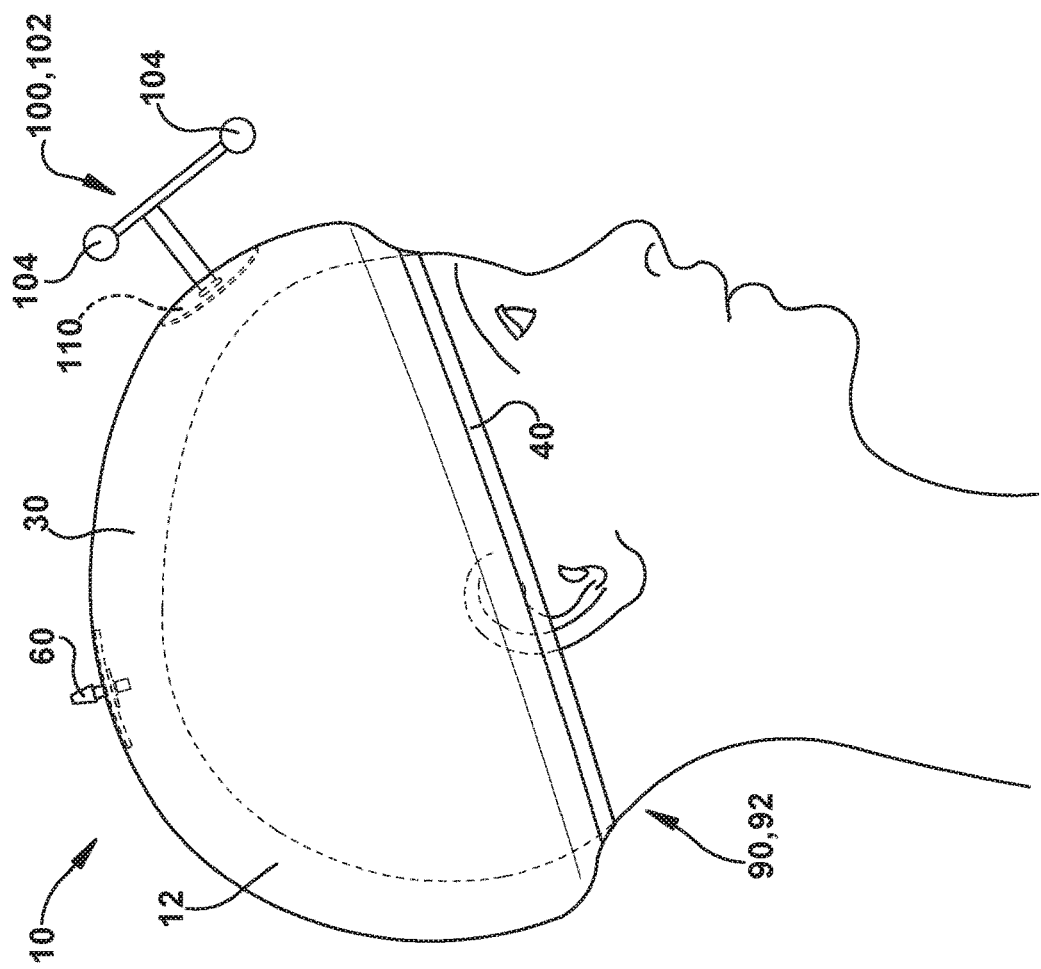
FIGS. 5A-5B illustrate the apparatus mounting a support structure in the form of an optical tracking fixture with fiducial markers according to one example implementation.
Figure 5A:
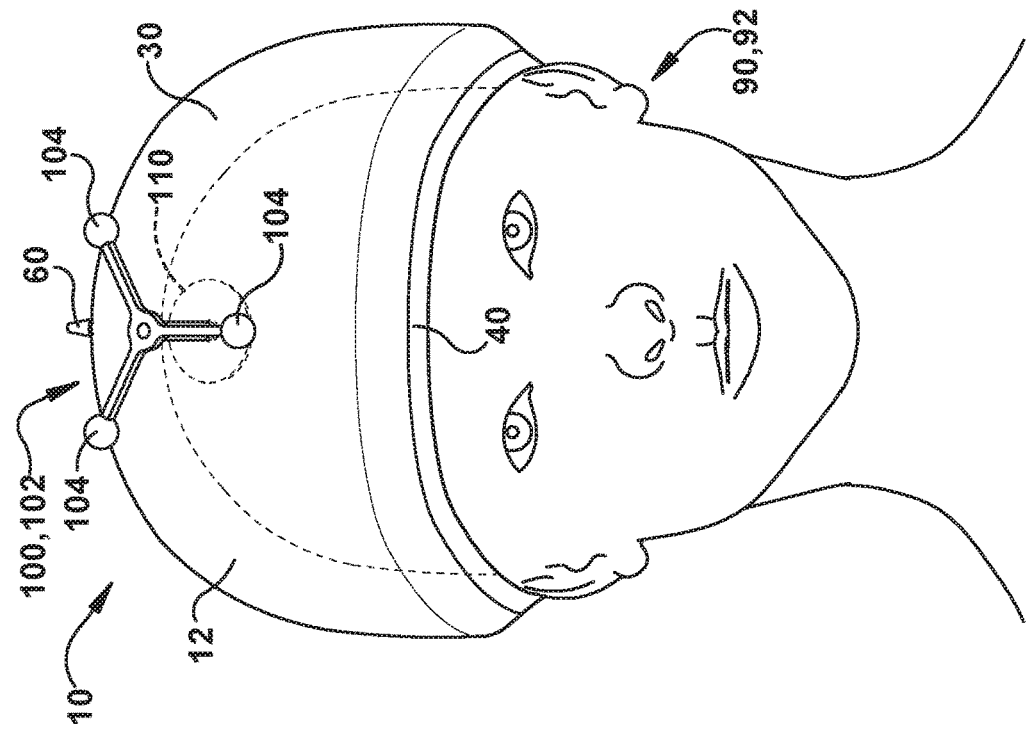

In the embodiment of FIGS. 1-2, the support structure 100 supported by the mounting apparatus 10, i.e., the cap 12, is a medical device in the form of a rigid body 102 that supports a plurality of target fiducials 104. This is shown in FIGS. 5A and 5B. The rigid body 102 can be secured to the cap 12 in a variety of manners. For example, the rigid body 102 can include a clamping mechanism 110 including overlying plates, such as circular or disc shaped plates, that are positioned on opposite sides of the outer cap layer 30. The clamping mechanism 110 can be secured to the outer cap layer 30 via a fastening connection, such as a threaded connection (e.g., nut and bolt/threaded stem). A seal can be provided, for example, via a gasket or a sealant (e.g., silicone), to prevent gas leakage where the rigid body 102 extends through the outer cap layer 30. The support structure 100 can also be installed prior to applying the connection that forms the seam 40.

The configuration, arrangement, and location of the rigid body 102 in FIGS. 5A and 5B is for purposes of illustration and is not meant to limit or restrict the configuration of the mounting apparatus 10. Those skilled in the art will appreciate that the support structure 100 can have various alternative configurations and arrangements without departing from the spirit and scope of the invention. Some of these alternatives are shown and described herein below.

In the example configuration of FIGS. 1-5, the mounting apparatus 10, i.e., the cap 12, is a granular jamming mounting apparatus that utilizes the granular jamming substance 50 to facilitate the rigid mount for the support structure 100. FIGS. 3A-3C illustrate a cross-sectional view of a portion of the cap 12 in various stages of use in providing the rigid mount for securing the support device 100 on the patient's head 92.

As shown in FIG. 3A, the granular jamming substance 50 occupies and fills or substantially fills the space of the confinement 44 between the inner and outer cap layers 20, 30. FIG. 3A illustrates the cap 12 in a pre-installed condition, before being placed on the patient's head 92. In this pre-installed condition, the granular jamming substance 50 has ample space to move freely within the confinement 44, and can move or flow fluidly to conform to the shape of the confinement. By "fluidly," it is meant that the mass granular jamming material 50 has no fixed shape and yields easily under the application of external forces and pressures, such as those experienced when the cap 12 is fitted onto the patient's head 92 or when the vacuum is applied to the cap.

The granular material 50, being one or more of the aforementioned silica granules, plastic/polymer beads, ceramic structures, glass structures, and/or coffee grounds, is a generally rigid, low density material that tends to move or flow easily under force into unoccupied spaces. In testing, it has been found that using coffee grounds as the granular material 50 can provide a good combination of weight, density, and the propensity to flow easily. The other materials—silica, plastics, polymers, ceramics, and glass—can be formed or otherwise produced to mimic or match these characteristics.

Referring to FIG. 3A with reference to FIGS. 1-2, to use the mounting apparatus 10, the cap 12 is positioned over, fitted and stretched onto the patient's head 92 in a manner much like a conventional cap, such as a swim cap, is fitted and stretched onto one's head. The cap 12 is adjusted onto the patient's head 92 until a close fit between the inner cap layer 20 and the head is established in a tight/snug manner. The cap 12 is also fitted and adjusted to position the support structure 100 and rigid body 102 in a desired location and orientation relative to the patient 90/patient's head 92.

The cap 12, when fitted onto the patient's head 92, is held in place due to the elastic constriction of the inner cap layer 20, which applies an inward elastic force on the patient's head. The material from which the inner cap layer 20 is constructed, e.g., silicone or latex rubber, can provide a good frictional engagement with the patient's head 92 and skin, providing grip that maintains the orientation of the inner cap layer 20 relative to the head. This condition of the cap 12 is shown in FIG. 3B.

Referring to FIG. 3B, as the cap 12 is fitted onto and stretched over the patient's head 92, the cap deforms and the granular material 50 becomes displaced and flows into the spaces created by this deformation. The granular material 50 flows into and fill gaps, voids, and other spaces in the confinement 44 and between the grains. As the granular material 50 flows, the cap 12 conforms to the shape of the patient's head 92. Since both the inner and outer cap layers 20, 30 are elastic in nature, both layers apply an inward elastic force on the patient's head 92. The inner cap layer 20 applies its inward elastic force directly onto the patient's head and thereby maintains the connection of the cap 12 with the head. The outer cap layer 30 applies its inward elastic force to the granular material 50 and to the patient's head 92 through the granular material.

Since this flow is not purely fluid in nature, the distribution of the granular material 50 in the confinement 44 can be manipulated by hand to make any desired adjustments. For example, the position of the support structure 100 can be manipulated to a desired position and orientation relative to the patient's head 92. The granular material 50 can then be manipulated to fill the space between the support structure 100 and the occupant's head 92 along with the granular material in the adjacent and surrounding space in order to maintain the position/orientation of the support structure. Advantageously, the elastic nature of the cap layers 20, 30 causes the cap 12 to elastically constrict onto the patient's head 92, which holds the granular material 50 and the support device 100 initially in place prior to applying the vacuum.

Even distribution and adequate thickness of the granular material 50 helps improve the overall strength of the jammed structure of the cap 14. If the jammed granular material 50 is too thin, the bending strength of the cap 12 material is severely decreased. If the jammed granular material 50 is too thick, the cap 12 becomes bulky without adding significant strength. To help maintain an even distribution of the granular material 50 about the confinement 44 of the cap 12, the granular material 50 can be formed with or include statically charged or magnetic particles. These statically charged or magnetic particles can repel each other, which can help the granular material to self distribute throughout the confinement 44 and around the cap 12.

At this point, with the cap 12 fitted onto the patient's head 92, initially secured via the elastic constriction and frictional engagement of the inner cap layer 20, and manipulated to the desired orientation of the support structure 100 and distribution of the granular material 50, the vacuum pump 64 is activated. The pump 64 removes air from within the confinement 44, creating a vacuum in the cap 12.

Referring to FIG. 3C, the vacuum causes the inner and outer layers 20, 30 of the cap 12 to be drawn-in and further compact the granular material 50. The elastic properties of the cap 12 cause it to conform closely to the shape and distribution of the volume of granular material 50. As the vacuum is drawn and the confinement 44 shrinks, the elastic nature of the cap 12 and the inward elastic forces applied by both the inner and outer cap layers 20, 30 causes the cap to maintain contact with and constrict onto the patient's head 92. These inward elastic forces also maintain the granular material formed against the contour of the patient's head 92 as the vacuum is drawn. Further, the elasticity of the cap layers 20, 30 take up any reduction in volume of the mass of granular material 50 that may result from compaction during the application of the vacuum. Because of this, the cap 12, when under vacuum, assumes a hardened rigid form, like that of a helmet, that matches the contour of the patient's head 92. The cap 12 thus provides a close fit that is custom tailored to the specific anatomy of the patient 90.

Referring to FIG. 1, the cap 12 provides a close secure fit that extends around and support the patient's head 92 in a cup-like manner. The cap 12 extends beyond the widest portion of the head 92 and converges inward, forming an interference fit of sorts. Put another way, the cap 12 extends around the patient's head 92 in a manner similar to the arrangement of a ball-and-socket joint in which the socket (i.e., the cap) extends beyond the equator of the ball (i.e., the head). The cap 12, extending around the patient's head 92 in this manner and with the vacuum applied to render the cap in a rigid form-fitting condition, secures the cap, and therefore the support structure 100, to the patient's head in a stable and secure manner.

Configured in this manner, the cap 12 is highly resistant to movement relative to the patient's head during surgical procedures. The apparatus 10 thus can provide a rigid and reliable support for the support structure 100 and, in the embodiment of FIGS. 1-5, the rigid body 102 and the tracking fiducials 104. The apparatus 10 can thus exhibit resistance to target registration errors (TREs) that are commensurate with, or even lower than, those associated with bone screw mounted rigid bodies.

The apparatus 10 is not limited to the support structure 100 supporting a rigid body 102 and/or target fiducials 104. The apparatus 10 can, for example, implement a support structure 100 for supporting a surgical tool. The surgical tool can be any device or instrument that may be required to perform a surgical task. For instance, the tool can be an endoscope for viewing a surgical field, a drill for accessing a target site in the anatomy, or a probe having tool ends, such as forceps, graspers, cutters, curettes, dissectors, scalpels, scissors, needles, drug delivery devices, ablation elements, drills, bone punches, suction/irrigation, etc. The tool can be manually or robotically operated, and can be adapted to perform any type of surgical operation where such tools may be useful, such as an endonasal surgical procedure.

Figure 6:
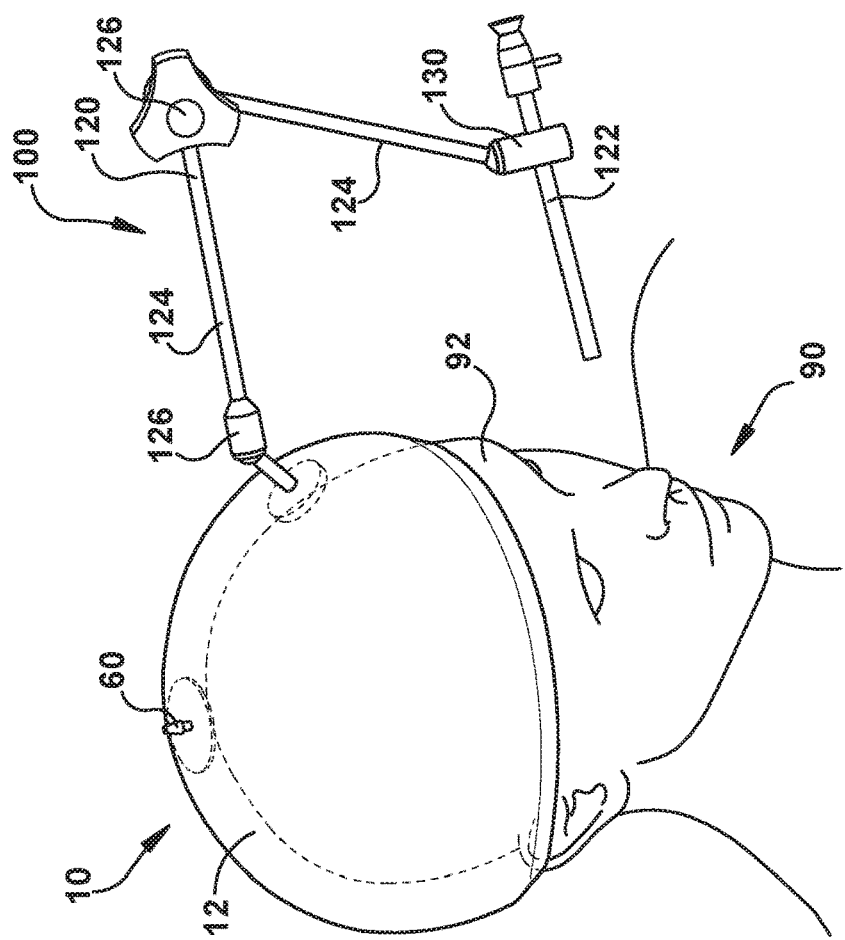
FIG. 6 illustrates the apparatus mounting a support structure in the form of a holder for supporting a surgical tool, such as an endoscope, in a desired position relative to the patient.

Referring to FIG. 6, in an example configuration of the apparatus 10, the support structure 100 is a surgical tool support 120 configured and adapted to support a surgical tool in the form of an endoscope 122. In this configuration, the support structure 100 can include one or more positioning arms 124 secured to each other at joints 126, such as pivot joints or ball and socket joints, that permit the support structure to be maneuvered relative to the patient 90. The joints 122 can include locking features that allow the arms 124 individually, and the support structure 100 in general, to be fixed in space relative to the patient's head 92. This, in combination with the rigid fixation of the cap 12 to the patient's head 92, provides for a rigid, reliable, and secure support for the surgical tool support 120.

The surgical tool support 120 also includes a tool receiver 130 that is configured and adapted to receive and secure, e.g., clamp onto, the endoscope 122 and support the endoscope in a desired position and orientation. Utilizing the surgical tool support 120, the surgeon can position the endoscope 122 in a desired position relative to the patient 92 in order to carry out the surgical procedure. The cap 12, being rigidly secured to the patient's head 92, allows for repositioning of the surgical tool support 120, if desired.

Figure 7:
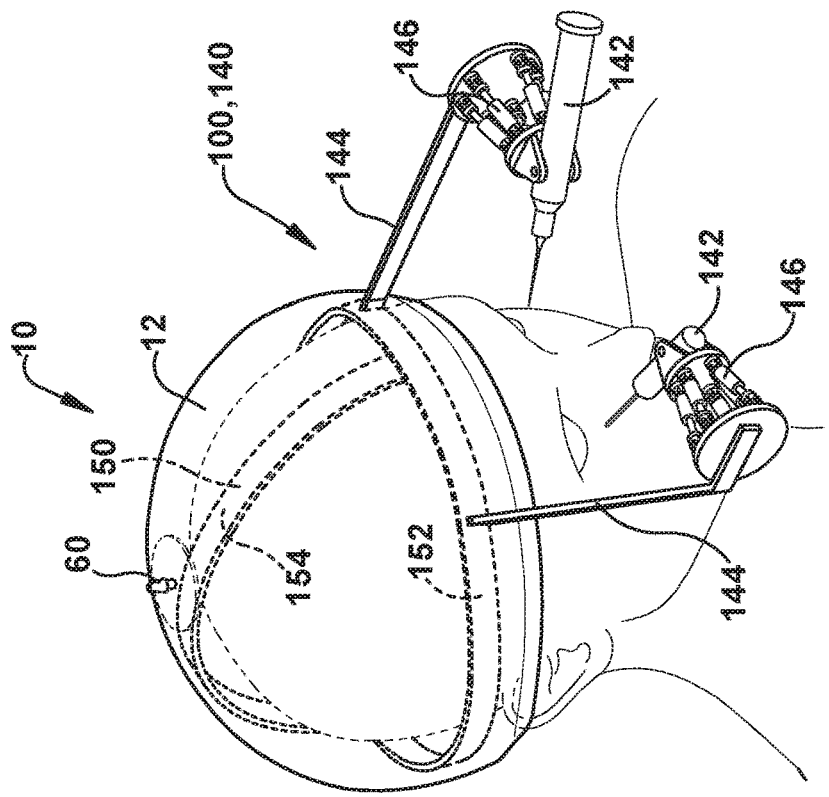
FIG. 7 illustrates the apparatus mounting a support structure in the form of a holder for supporting a surgical robot in a desired position relative to the patient.

Referring to FIG. 7, in another example configuration of the apparatus 10, the support structure 100 is a surgical robot support 140 configured and adapted to provide rigid non-invasive support of a surgical tool in the form of one or more surgical robotic devices 142. In the example configuration of FIG. 7, there are two surgical robotic devices 142. The apparatus 10 could, however, be configured to receive either surgical robotic device 142 individually or in combination, as shown.

In the configuration of FIG. 7, the support structure 100 includes positioning arms 144 that support the surgical robotic devices 142. The positioning arms 144 can be unitary in construction as shown or can have a multi-arm, maneuverable configuration, secured to each other at joints and including locking features in a manner similar or identical to the arms illustrated in the example configuration of FIG. 6.

In the example configuration of FIG. 7, the surgical robot support 140 is a dual arm microsurgery robot support for ophthalmic applications. The support structure 100 can, of course, be adapted to support other types of surgical robots. As shown in the example configuration of FIG. 7, the support structure 140 can include a Stuart-Gough style robotic platform 146. Advantageously, this platform 146 can provide six degrees of freedom—x, y, z axis linear movement, and pitch, roll, and yaw rotational movement, which increases the dexterity and positioning of the surgical robotic devices 142 in a small space.

In the example configuration of FIG. 7, the support structure 100 includes a frame 150 that is positioned in the confinement 44 of the cap 12 and surrounded by the granular material 50. The frame 150 can include a band portion 152 that encircles the patient's head 92. One or more span portions 154 can extend over the patient's head and have opposite ends connected to the band portion 152. The frame 150, extending around and over the patient's head 92, can provide a rigid secure structure or foundation from which to support the positioning arms 144 and the robots 142. This can be advantageous, for example, where the support structure 100 supports a medical device that has an increased weight.

Figure 8:
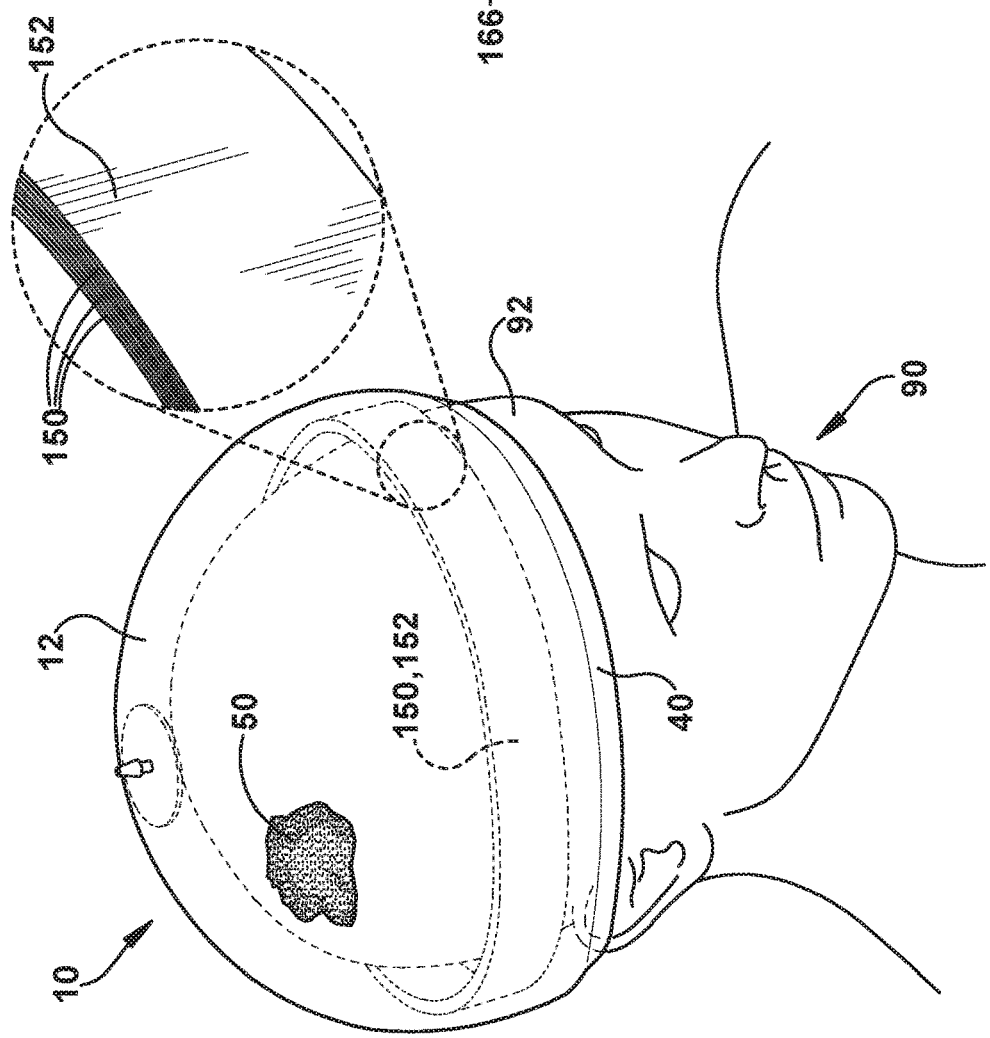

Another example configuration of the apparatus 10 is illustrated in FIG. 8. The embodiment of FIG. 8 is similar to the example embodiments of FIGS. 1-7. According to the example embodiment of FIG. 8, the apparatus 10 can include jamming materials in place of, or in addition to, the granular material 50. In the embodiment of FIG. 8, the apparatus 10 includes jamming sheets of material 150, such as paper (e.g., 20 lb. bond paper), sandpaper, or thin plastic (e.g., polyester film), that are positioned within the confinement 44. In the example configuration of FIG. 8, the jamming sheets 150 are thin strips of material arranged in a loop or band 152 that encircles the patient's head 92 in the manner, for example, of a headband.

Prior to applying the vacuum, the sheets of material 150 can slide relative to each other. When the cap 12 is fitted onto the patient's head 92, the band 152 of jamming sheets 150 are pressed against and conform to the contour of the patient's anatomy and are pressed against one another. Upon drawing a vacuum in the cap 12, the jamming sheets 150 are further urged against one another and lock due to friction between the sheets. This friction lock maintains the assumed shape of the band 152, allowing the jamming sheets 150 to help support the medical device(s) supported by the cap 12.

Granular jamming via the granular material 50 does well to conform to the surface of the body and exhibits strong compressive strength. The granular material structure, even when hardened under vacuum, has comparatively low tensile strength. Advantageously, the jamming sheets 150, when under vacuum, can have a comparatively higher tensile strength. Thus, implementing both the jamming sheets 150 and granular material 50 in the cap 12 can provide both high compressive and tensile strength.

In a configuration of the cap 12 in which the band 152 is implemented in addition to the granular material 50, the band can serve to improve the fit and reliability with which the cap is held on the patient's head 92. For example, as shown in FIG. 8, the band 152 can be positioned in the confinement 44 to extend adjacent or near the seam 40. The band 152 can thus serve to maintains a lower rim 14 of the cap 12 secured to the patient 90 and can help provide enhanced tensile strength in that region of the cap.

Advantageously, the material (e.g., paper or plastic) that is used to form the sheets 150 can be an inelastic material. Thus, the band 152 forming, supporting, or otherwise bolstering the rim portion 14 of the cap 12, can be made to have an inelastic quality when the vacuum is formed. This can be somewhat different than a cap 12 that omits the band 152. In those constructions, it is the material of the cap layers 20, 30, which is elastic in nature, that forms the rim 14. Although the vacuum can substantially prohibit stretching of the rim 14, the inclusion of the band 152 will improve the resistance of the rim to stretching once the vacuum is applied.

Figure 9:
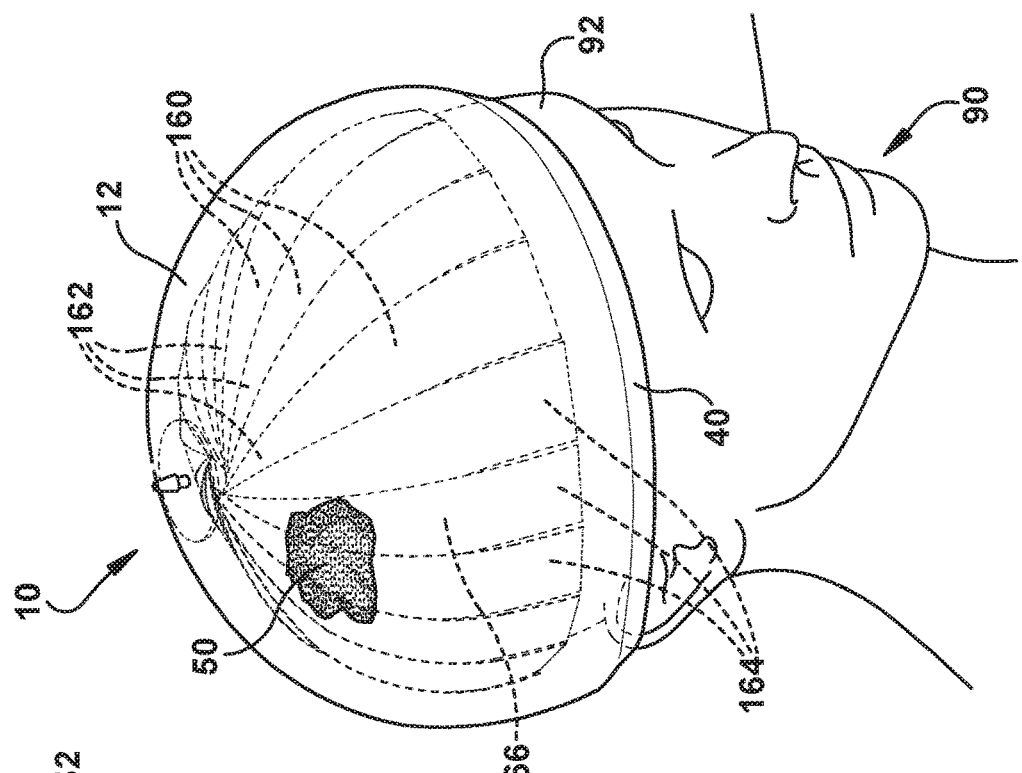

Another example configuration of the apparatus 10 is illustrated in FIG. 9. The embodiment of FIG. 9 is similar to the example embodiment of FIG. 8 in that the cap 12 includes jamming sheets of material 160, such as paper or thin plastic, that are positioned within the confinement 44. In the example configuration of FIG. 9, the jamming sheets 160 are sheets of material that are fanned out in a domed pattern that follows the contour of the cap 12. The sheets 160 can, for example, have a tapered or generally triangular configuration with narrow portions 162 positioned overlying a top-center portion of the domed pattern and wide portions 164 positioned extending about the lower periphery of the domed pattern, adjacent or near the seam 40. In this configuration, the jamming sheets 160 form a jamming sheet cap 166 within the cap 12.

When the cap 12 is fitted onto the patient's head 92, the cap 166 of jamming sheets 160 are pressed against and conform to the contour of the patient's anatomy and are pressed against one another. Upon drawing a vacuum in the cap 12, the jamming sheets 160 are further urged against one another and lock due to friction between the sheets. This friction lock maintains the assumed shape of the cap 166, allowing the jamming sheets 160 to help support the medical device(s) supported by the cap 12.

In a configuration of the cap 12 in which the jamming sheet cap 166 is implemented in addition to the granular material 50, the sheets 160 can serve to improve the fit and reliability with which the cap 12 is held on the patient's head 92. Advantageously, the material (e.g., paper or plastic) that is used to form the sheets 160 can be an inelastic material. Thus, the jamming sheet cap 166 can support or otherwise bolstering the cap 12. The jamming sheet cap 166 can be made to have an inelastic quality when the vacuum is formed. This can be somewhat different than a cap 12 that omits the sheets 160 and includes jamming material 50 alone. In those constructions, the material of the cap layers 20, 30 is elastic in nature. Although the vacuum can substantially prohibit stretching of the cap 12, the inclusion of the jamming sheet cap 166 will improve the resistance of the rim to stretching once the vacuum is applied.

Additional example configurations of the apparatus 10 are illustrated in FIGS. 10 and 11. The example configurations of FIGS. 10 and 11 is similar to the example embodiment of FIGS. 1-7. In the example configurations of FIGS. 10 and 11, the cap 12 includes a mesh material 180 that can helps strengthen the cap under vacuum and/or limit the extent to which the granular material 50 can move or flow within the confinement 44.

In FIG. 10, the mesh material 180 can be one or more layers 182 of mesh material that have an open mesh size that is greater than the grain size of the granular material 50. In this configuration, the mesh layer(s) 182 are reinforcing layers that help improve the structural integrity of the cap 12 when the vacuum is applied. When the vacuum is applied, the granular material 50 has a comparatively high compression strength, but can have a comparatively low tensile strength. The mesh layer(s) 182 can be constructed of a material, such as nylon, polyester, aramid fiber materials, etc. that exhibits a high tensile strength. When the vacuum is applied, the granular material 50 compresses onto and around the mesh layer(s) 182 and the structure hardens. The mesh layer(s) 182, being encased and embedded in the granular material 50, lends its tensile strength to the hardened structure of the cap 12 and thereby increases the tensile strength of the cap.

In FIG. 11, the mesh material 180 forms multiple compartments 184 in a quilt-like manner in which the mesh sheets 180 are interconnected to form compartmental boundaries 186. In FIG. 11, the open mesh size within the individual compartments 184 is smaller than the grain size of the granular material 50. The compartments 184 thus contain the granular material 50 and help control the distribution of the granular material 50 in the confinement 44 of the cap 12. This can help prevent unwanted shifting or flowing of the granular material 50 prior to applying the vacuum. Like the mesh layers 182 of FIG. 10, the mesh material 180 used to form the compartments 184 can be constructed of a material, such as nylon, polyester, aramid fiber materials, etc. that exhibits a high tensile strength. When the vacuum is applied, the granular material 50 compresses onto and around the mesh forming the compartments 184 and the structure hardens. The mesh material of the compartments 184, being encased and embedded in the granular material 50, lends its tensile strength to the hardened structure of the cap 12 and thereby increases the tensile strength of the cap.

Figure 12:
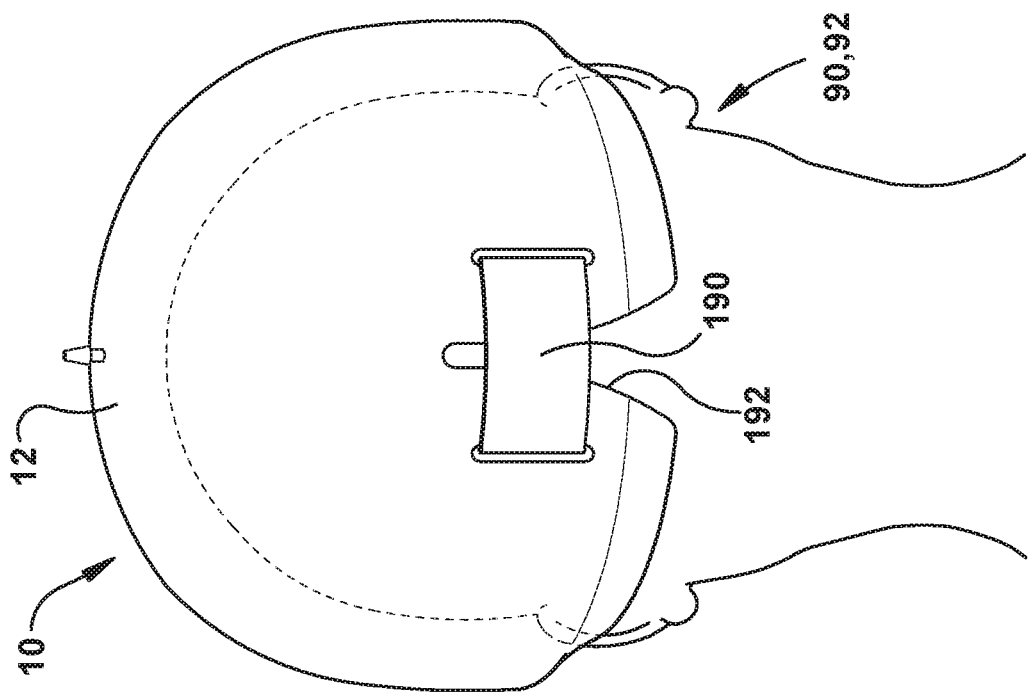
FIG. 12 illustrates an example configuration of a mounting apparatus including an additional retention feature.

Another example configuration of the apparatus 10 is illustrated in FIG. 12. The example configuration of FIG. 12 is similar to the example embodiment of FIGS. 1-7. In the example configuration of FIG. 12, the cap 12 includes an elastic strap 190 that assists in fitting the cap to the patient's head 92. The cap 12 also includes a slit 192 across which the strap 190 extends. The slit 192 permits the lower rim 14 of the cap 12 to expand more freely so as to facilitate fitting the cap onto the patient's head 92. To this end, the strap 190 can be configured to permit loosening for fitting the cap 12 onto the head 92 and tightening thereafter to secure the cap in place. This can be facilitated, for example, via a buckle or a hook and loop (Velcro®) fastening structure.

Figure 13:
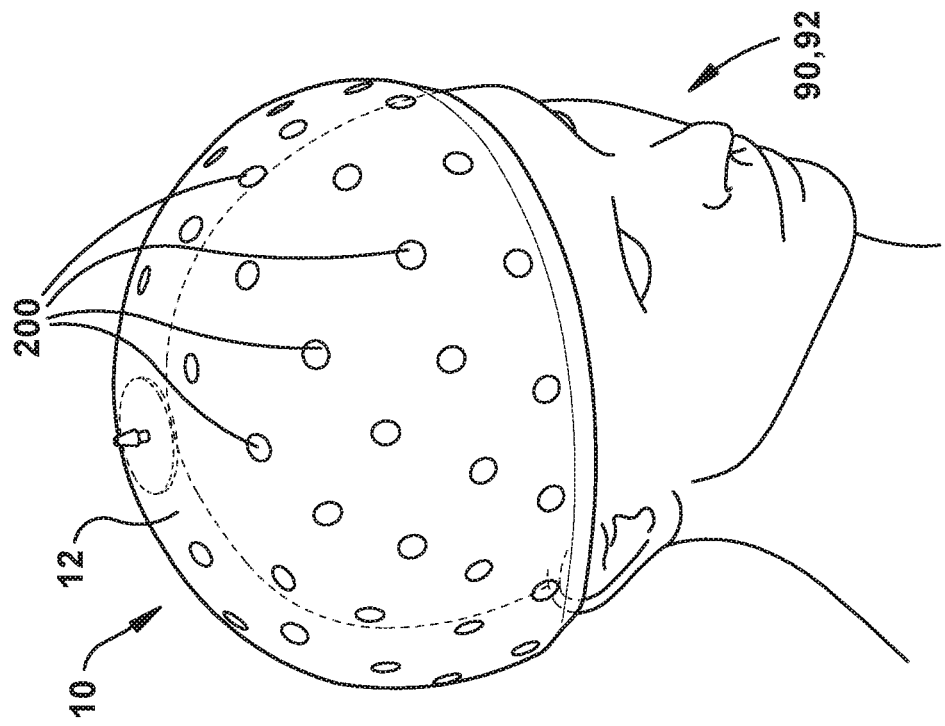
FIG. 13 illustrates an example configuration of the mounting apparatus including an integrated medical device.

Another example configuration of the apparatus 10 is illustrated in FIG. 13. The example configuration of FIG. 13 is similar to the example embodiment of FIGS. 1-7. In the example configuration of FIG. 13, the cap 12 supports target fiducials 200 similar to those illustrated in the example configurations of FIGS. 1-7. In the configuration of FIG. 13, however, instead of including a rigid body upon which the fiducials are supported, the target fiducials 200 are fixed directly to the outer cap layer 30 of the cap 12. In the example configuration of FIG. 13, the number, spacing, and arrangement of the target fiducials 200 are shown for purposes of illustration only. The cap 12 can include any desired number of target fiducials 200 arranged and spaced in any desired configuration.

In one example configuration, the target fiducials 200 can be stickers or adhesive-backed target fiducials that are pre-applied to the cap 12 or applied after the cap 12 is fitted onto the patient's head 92. Fitting the cap 12 with the target fiducials 200 after fitting can allow for positioning the patient's head 92 and/or the surgical imaging system at ideal relative locations. This can be particularly well-suited for surgical optical tracking systems where fiducial markers can be applied and scanned on the fly, such as the NDI Krios® system. As another example, the target fiducials 200 can be fixed to the cap 12 by embedding the fiducials in the outer cap layer 30.

From the above, it will be appreciated that the invention provides a non-surgically attached stable platform for supporting rigid body fiducial mounts and/or surgical tools during surgery. Although specific locations of these devices are depicted in the figures, the apparatus could be configured to position the devices at any desired location on or relative to the patient's head.

While example embodiments have been presented in the foregoing detailed description, it should be appreciated that variations of these embodiments can exist without departing from the spirit and scope of the invention. The embodiments described herein are not intended to limit the scope, applicability, or configuration of the invention. Rather, the detailed description provides sufficient detail to enable one skilled in the art to make and use the invention. Those skilled in the art will perceive applications, improvements, changes and modifications to the invention. Such applications, improvements, changes and modifications within the skill of the art are intended to be covered by the appended claims.

The invention claimed is:

1. An apparatus for supporting a medical device on a patient, the apparatus comprising: a mounting structure configured to be fitted onto the patient to encircle at least a portion of a body part of the patient, the mounting structure comprising an inner layer and an outer layer that define a confinement; a jamming material contained within the confinement, wherein the jamming material is configured to flow within the confinement to conform to the shape of the body part of the patient onto which the mounting structure is fitted, and wherein a mass of jamming material is configured to harden and become rigid in its conformed shape in response to a vacuum being formed in the confinement; and a support structure adapted to receive and support the medical device, the support structure having a portion disposed in the jamming material in the confinement so that the jamming material provides a hard, rigid support of the support device in response to the vacuum being formed in the confinement.

2. The apparatus recited in claim 1, wherein the inner layer is positioned within an inner space defined by the outer layer, and wherein overlying peripheral edge portions of the inner and outer layers are interconnected to seal the jamming material in the confinement.

3. The apparatus recited in claim 1, wherein the inner and outer layers are constructed of a substantially airtight material.

4. The apparatus recited in claim 3, wherein the airtight material comprises a material that is at least one of elastomeric and deformable.

5. The apparatus recited in claim 1, wherein the inner layer of the mounting structure is constructed of a deformable material that conforms to the patient's anatomy when fitted onto the patient.

6. The apparatus recited in claim 5, wherein the outer layer of the mounting structure is constructed of a material that applies an inward elastic force that causes the jamming material to conform to the shape and contour of the body part onto which the mounting structure is fitted.

7. The apparatus recited in claim 1, wherein the mounting structure is adapted to be fitted onto a patient's head.

8. The apparatus recited in claim 1, wherein the jamming material comprises a granular jamming material.

9. The apparatus recited in claim 8, wherein the granular jamming material comprises at least one of silica granules, plastic beads, polymer beads, ceramic structures, glass structures, and coffee grounds.

10. The apparatus recited in claim 1, wherein the jamming material comprises overlying sheets of material.

11. The apparatus recited in claim 10, wherein the sheets of material comprise at least one of paper, sandpaper, and thin plastic sheets.

12. The apparatus recited in claim 10, wherein the sheets of material are strips of material arranged in a multilayer loop.

13. The apparatus recited in claim 12, wherein the multilayer loop extends around an annular rim portion of the mounting structure.

14. The apparatus recited in claim 10, wherein the sheets of material are arranged in overlying sheets arranged to form a multilayer dome of sheet material.

15. The apparatus recited in claim 1, wherein the support structure comprises a structure for supporting one or more target fiducials for an optical scanning system.

16. The apparatus recited in claim 1, wherein the support structure comprises a structure for holding a surgical tool comprising at least one of an endoscope, a drill, a probe, forceps, graspers, cutters, curettes, dissectors, scalpels, scissors, needles, drug delivery devices, ablation elements, bone punches, and suction/irrigation devices.

17. The apparatus recited in claim 1, wherein the jamming material comprises a granular jamming material, wherein the support structure comprises a frame structure disposed within the confinement and having portions surrounded by the granular jamming material.

18. The apparatus recited in claim 1, wherein the medical device is adapted to be fixed directly to an outer surface of the outer layer by at least one of bonding the medical to the outer surface with an adhesive and embedding the medical device to the outer layer.

19. The apparatus recited in claim 18, wherein the medical device comprises a target fiducial.

20. The apparatus recited in claim 1, wherein the lamming material comprises a granular lamming material, the apparatus further comprising a mesh material disposed in the confinement and at least partially surrounded by the granular material.

21. The apparatus recited in claim 20, wherein the mesh material has an open mesh size larger than a grain size of the granular material.

22. The apparatus recited in claim 20, wherein the mesh material has an open mesh size smaller than a grain size of the granular material, and wherein the mesh material is compartmentalized to define compartments that contain the granular material.

23. The apparatus recited in claim 1, further comprising a flexible elongated member, such as a strap, for helping to secure the mounting structure to the patient.

24. The apparatus recited in claim 23, wherein the mounting structure comprises a slit extending vertically from a rim of the mounting structure, and wherein the flexible elongated member extends across the slit and draws portions of the mounting structure on opposite sides of the slit together.

25. The apparatus recited in claim 1, wherein the mounting structure comprises a cap, the inner layer comprising an inner cap layer and the outer layer comprising an outer cap layer, wherein the inner cap layer and outer cap layer each have a concave structure, the inner cap layer being positioned within an inner space defined by the outer cap layer, and overlying peripheral edge portions of the inner and outer cap layers being interconnected to seal the jamming material in the confinement.

26. An apparatus for supporting a medical device on a patient, the apparatus comprising: a mounting structure configured to be fitted onto the patient to encircle at least a portion of a body part of the patient, the mounting structure comprising an inner layer and an outer layer that define a confinement; a jamming material contained within the confinement, wherein the jamming material is configured to flow within the confinement to conform to the shape of the body part of the patient onto which the mounting structure is fitted, and wherein the mass of jamming material is configured to harden and become rigid in its conformed shape in response to a vacuum being formed in the confinement wherein the jamming material comprises a granular jamming material; and a mesh material disposed in the confinement and at least partially surrounded by the granular material, wherein the mesh material has an open mesh size larger than a grain size of the granular material.

* * * * *

UNITED STATES PATENT AND TRADEMARK OFFICE
CERTIFICATE OF CORRECTION

PATENT NO. : 11,974,889 B2
APPLICATION NO. : 16/347634
DATED : May 7, 2024
INVENTOR(S) : Patrick Wellborn et al.

It is certified that error appears in the above-identified patent and that said Letters Patent is hereby corrected as shown below:

In the Claims

Column 16, Claim 20, Line 10, delete "lamming" and insert --jamming--, therefor.
Column 16, Claim 20, Line 11, delete "lamming" and insert --jamming--, therefor.

Signed and Sealed this
Sixteenth Day of July, 2024

Katherine Kelly Vidal
Director of the United States Patent and Trademark Office